US006322786B1

(12) United States Patent
Anderson

(10) Patent No.: US 6,322,786 B1
(45) Date of Patent: Nov. 27, 2001

(54) METHOD OF PRODUCING BONE-INDUCING AGENT

(75) Inventor: H. C. Anderson, Shawnee Mission, KS (US)

(73) Assignee: Kansas University Medical Center Research Institute, Inc., Kansas City, KS (US)

( * ) Notice: Subject to any disclaimer, the term of this patent is extended or adjusted under 35 U.S.C. 154(b) by 0 days.

(21) Appl. No.: 08/799,343

(22) Filed: Feb. 13, 1997

Related U.S. Application Data

(60) Provisional application No. 60/011,703, filed on Feb. 15, 1996.

(51) Int. Cl.$^7$ .................................................. A61K 35/66
(52) U.S. Cl. .............................. 424/115; 514/2; 514/21; 424/573; 435/366
(58) Field of Search ....................... 514/2, 21; 424/573, 424/115; 435/366

(56) References Cited

U.S. PATENT DOCUMENTS 6,020,313 * 2/2000 Anderson et al. ..................... 514/21

OTHER PUBLICATIONS

Amitani, K., et al., *Gann.*; 66:327–329,1975.
Anderson, H.C., et al., *Am. J. Path.*; 44:507–519, 1964.
Anderson, H.C., et al., *Fed. Proc.*; 27:475, 1968.
Anderson, H.C., et al., *J. Cell Biol.*; 41:59–72, 1969.
Anderson, H.C., et al., *Bone and Min.*; 16:49–62, 1992.
Anderson, H.C., *Cur. Opin. Ther. Patents*; 4:17–29, 1994.
Anderson, H.C., et al., *Clin. Orthop. Rel. Res.*; 313:129–134, 1995.
Bentz, H., et al., *Matrix*; 11:269–275, 1991.
Chen, T.L., et al., *J. Bone Min. Res.*; 6:1387–1393, 1991.
Cook, S.D., et al., *Spine*; 19:1655–1663, 1994.
Dale, L., et al., *Develop.*; 115:573–585, 1992.
Elima, K., *Ann. Med.*; 25:395–402, 1993.
Fogh, J., et al. In: *Human Tumor Cells In Vitro*, J. Fogh Ed., Plenum, N.Y. pp. 115–159. 1975.
Francis–West, P.H., et al., *Develop. Biol.*; 201:168–178, 1994.
Fukagawa, M., et al., *Develop. Biol.*; 163: 175–183, 1994.
Gerhart, T.N., et al., *Clin. Orthop. Rel. Res.*; 293:317–326, 1993.
Hammonds, R.G., et al., *Molec. Endocrinol.*; 5:149–155, 1991.
Harland, R.M., *Proc. Nat. Acad. Sci.*; 91:10243–10246, 1994.
Hollinger, J., et al., *J. Oral Maxillofac. Surg.*; 47:1182–1186, 1989.
Hunt, T.R., et al., *J. Bone Jt. Surg.*; 78A:41–48, 1996.
Jones, C.M., et al., *Develop.*; 111:531–542, 1991.
Johnson, E.E., et al., *Clin. Orthop. Rel. Res.*; 277:229–237, 1992.
Katagiri, T., et al., *Biochem. Biophys. Res. Comm.*; 172:295–299, 1990.
Lovell, T.P., et al., *Clin. Orthop. Rel. Res.*; 243:266–274, 1989.
Lyons, K.M., et al., *Genes and Develop.*; 3:1657–1668, 1989.
Lyons, K.M., et al., *Develop.*, 109:833–844, 1990.
Luyten, F.P., et al., *J. Biol. Chem.*; 264:13377–13380, 1989.
Masahara, K., et al., *Bone*; 16:91–96, 1995.
Nakase, T., et al., *J. Bone Min. Res.*; 9:605–610, 1996.
Raval, P., et al., *J. Orthop. Res.*; 14:180, 1993.
Raval, P., et al., *J. Dent. Res.*; 75:1518–1523, 1996.
Rickard, D.J., et al., *Develop. Biol.*, 161:218–228, 1994.
Ripamonte, V., et al., *Matrix*; 12:369–380, 1992.
Sampath, T.K., et al., *J. Biol. Chem.*; 265:13198–13205, 1990.
Staehling–Hampton, K., et al., *Cell Growth & Diff.*; 5:585–593, 1994.
Suzuki, A., et al., *Proc. Nat. Acad. Sci.*; 37:581–588, 1995.
Takaoka, K., et al., *Clin. Orthop. Rel. Res.*; 164:265–270, 1982.
Takaoka, K., et al., *Clin. Orthop. Rel. Res.*; 292:329–336, 1993.
Takuwa, Ohse, G., et al. *Biochem. Biophys. Res. Comm.*; 174:96–101, 1991.
Thies, R.S., et al., *Endocrinol.*; 130:1318–1324, 1992.
Toriumi, D.M., et al., *Head Neck Surg.*; 117:1101–1112, 1992.
Urist, M.R., et al., *Proc. Soc. Exp. Biol. & Med.*; 173:194–199, 1983.
Vukicevik, S., et al., *Biochem. Biophys. Res. Comm.*; 166:750–756, 1990.
Vukicevik, S., et al., *Biochem. Biophys. Res. Comm.*; 198: 693–700, 1994.
Vukicevik, S., et al., *J. Histochem. Cytochem.*; 42:869–875, 1994.
Wang, E.A., et al., *Proc. Nat. Acad. Sci.*(USA); 87:2220–2224, 1990.
Wozney, J.M., et al., *Exp. Pharm.*; 107:723–748, 1993.
Yamaguchi, A., et al., *J. Cell Biol.*; 113:681–687, 1991.
Yasko, A.W., et al., *J. Bone Jt. Surg.*; 74A:659–670, 1992.

* cited by examiner

*Primary Examiner*—Jean C. Witz
(74) *Attorney, Agent, or Firm*—Hovey, Williams, Timmons & Collins

(57) ABSTRACT

The present invention provides methods to isolate and purify components required for bone-induction using extracts of Saos-2 cells or proteins released by Saos-2 cells into conditioned tissue culture medium. In addition, the present invention provides a method of augmenting bone growth locally comprising implanting the near osteoprogenitor cells the bone inducing agent isolated in the methods of the present invention, together with a mechanically suitable biodegradable carrier.

18 Claims, 5 Drawing Sheets

(1 of 5 Drawing Sheet(s) Filed in Color)

METHOD OF PRODUCING BONE-INDUCING AGENT

This application claims the benefit of U.S. provisional application No. 60/011,703, filed on Feb. 15, 1996.

FEDERAL FUNDING LEGEND

This invention was funded in part by NIH Grant DE05262. The U.S. Government, therefore, has certain rights in this invention.

BACKGROUND OF THE INVENTION

1. Field of the Invention

The present invention relates generally to the fields of the biology of bone formation and protein chemistry. More specifically, the present invention relates to a novel method of producing bone-inducing agent by cultured human osteosarcoma cells.

2. Description of the Related Art

In recent years a number of purified bone-inducing proteins have been isolated, sequenced, and produced by recombinant technology using transfected animal tissue culture cells. These molecules are designated bone morphogenetic proteins (BMPs) 1 through 9, or, alternately, "osteogenin" which is identical to BMP-3 (27), and "osteoinductive protein-1" which is identical to BMP-7 (34). All the bone morphogenetic proteins (except BMP-1) have molecular structures similar to transforming growth factor-$\beta$ (TGF-$\beta$) (47).

Several of the bone morphogenetic proteins are expressed at specific tissue sites and at specific stages of embryonic development (21). Early in embryogenesis, BMP-1 and BMP-4 are expressed in the central mesoderm and appear to play a role in dorso-ventral patterning (11,15,18,35,36). BMP-2, BMP-3, BMP-4, BMP-6, and BMP-7 mRNAs and proteins have been localized in the craniofacial mesenchyme, in developing limb buds and in tooth germs of mouse embryos (12,14,21,25,26,44,45) suggesting an important role for these bone morphogenetic proteins in cartilage and bone formation during embryogenesis. In fracture healing, BMP-4 mRNA is expressed by pre-osseous bone repair cells (29). Therefore, it is logical to predict that one or more of the bone morphogenetic proteins may be utilized in future therapy to promote normal craniofacial development or stimulate bone replacement or fracture repair.

Each of the bone morphogenetic proteins can induce bone formation in soft tissues when implanted subcutaneously in combination with extracted bone matrix, an incompletely-defined substance, which is believed to function as a slow release vehicle for bone morphogenetic protein. However, the possibility remains that trace amounts of one or more osteoinductive cofactors may persist in the extracted bone matrix and interact with exogenously added single bone morphogenetic proteins to induce bone (6). Semi-purified preparations of bone morphogenetic protein (19,20,22,24, 33) and recombinant forms of BMP-2 or BMP-7 (10,16,41, 49) mixed with bone matrix carrier have been reported to augment bone repair when implanted directly into bone defects.

Most of the bone morphogenetic proteins were isolated initially from large quantities of decalcified bovine bone (42). Once the primary structure of each bone morphogenetic protein was determined, production of recombinant bone morphogenetic proteins was achieved by transfecting Chinese hamster ovary (CHO) cells or other transformed animal cell lines with full length transcripts of human cDNA for bone morphogenetic proteins 1–7 (17,46) to initiate synthesis of bone morphogenetic proteins. Many investigators in the field would predict that a recombinant form of a single bone morphogenetic protein will ultimately be the best product for human clinical usage. However, there are drawbacks to this method of production, e.g., there may be residual, sensitizing hamster cell proteins contaminating the purified recombinant secretory product, or more than one pure bone morphogenetic protein may have to be combined (8) with other cofactors (such as may be present in bone matrix carrier) in order to maximally stimulate bone regeneration.

An alternative source of bone-inducing activity can be found in certain cultured cells. These include human amniotic cells (2), Hela cells (3), and, in recent years, osteoinductivity has been identified in murine (1,37) and human (5,6) osteosarcoma cells. However osteosarcoma cells that can induce bone are very unusual (5). Amitani, et al. (1) adapted the osteoinductive BFO strain of the Dunn murine osteosarcoma to cell culture, and Takaoka, et al. have shown that murine BFO cells express considerable quantities of BMP-4 (38). A bone-inducing agent is present in Saos-2 human osteosarcoma cells (5), but other osteosarcoma cell lines are non-osteoinductive (30,31) when compared to Saos-2 cells in a similar bioassay. Thus, Saos-2 cells are unique among cultured human bone cells in being able to elaborate a bone-inducing, morphogenetic agent.

The prior art is deficient in the lack of effective means of producing bone-inducing agents. The present invention fulfills this long-standing need and desire in the art.

SUMMARY OF THE INVENTION

The present invention isolates and purifies essential components required for bone-induction using extracts of Saos-2 cells or proteins released by Saos-2 cells into conditioned tissue culture medium. One object of the present invention is to purify biochemically the bone-inducing agent present within Saos-2 cells using sequential chromatography.

Another specific object of the present invention is to purify osteoinductive proteins that are secreted by Saos-2 cells and released thereby into serum-free conditioned culture medium. The present invention demonstrates that proteins secreted into the culture medium by Saos-2 cells are bone-inducing when implanted subcutaneously into Nu/Nu immunoincompetent mice.

In one embodiment of the present invention, there is provided a method of isolating a bone inducing agent in vitro, comprising the steps of: growing Saos-2 cells; harvesting said Saos-2 cells; pelleting said Saos-2 cells; washing said Saos-2 cells in acetone; drying said Saos-2 cells; dissolving said Saos-2 cells in GuHCl; centrifuging said dissolved Saos-2 cells at about 10,000 g to produce a pellet and a supernatant; running said supernatant through a Sephacryl 200 column in GuHCl to produce a first eluate; collecting fractions of said first eluate; pooling said fractions of said first eluate to produce a first pooled protein fraction, wherein said fractions pooled contain a highest bone inducing activity; dialyzing said first pooled protein fraction against about 6M urea to produce a first dialysate; running said first dialysate through an anion or cation exchange column to produce a second eluate; collecting fractions of said second eluate; pooling said fractions of said second eluate to produce a second pooled protein fraction, wherein said fractions pooled contain a highest bone inducing activity; running said a second pooled protein fraction through a Heparin/Sepharose column to produce a third eluate; collecting fractions of said third eluate; pooling said fractions of said third eluate to produce a third pooled protein fraction, wherein said fractions pooled contain a highest bone inducing activity; dialyzing said third pooled protein fraction to produce a second dialysate; applying said second dialysate to an HPLC column; eluting said second dialysate by an acetonitrile gradient; collecting fractions of said second dialysate; and pooling said fractions of said second dialysate to produce a fourth pooled protein fraction, wherein said fractions pooled contain isolated bone inducing agent.

Another embodiment of the present invention provides a method of isolating a bone inducing agent in vitro, comprising the steps of: growing Saos-2 cells to confluence in an appropriate cell culture medium with serum; removing said cell culture medium with serum; washing said Saos-2 cells; adding an appropriate cell culture medium without added serum; incubating said Saos-2 cells for about 48 hours; collecting said cell culture medium without added serum; and filtering said cell culture medium without added serum through a 0.45 micron pore filter to produce a filtrate and a retentate; wherein said retentate contains said isolated bone inducing agent. A particular embodiment of this method further includes the steps of: solublizing said retentate in about 6M urea and dialyzing said solublized retentate against water to produce dialyzed retentate.

Another object of the present invention provides a method of augmenting bone growth locally comprising implanting the bone inducing agent isolated in the above-detailed methods, together with a mechanically suitable biodegradable carrier, near osteoprogenitor cells selected from the group of marrow, periosteum and endosteum.

Other and further aspects, features, and advantages of the present invention will be apparent from the following description of the presently preferred embodiments of the invention given for the purpose of disclosure.

BRIEF DESCRIPTION OF THE DRAWINGS

The patent or application file contains at least one photograph executed in color. Copies of this patent or patent application publication with color photograph will be provided by the Office upon request and payment of the necessary fee.

So that the matter in which the above-recited features, advantages and objects of the invention are attained and can be understood in detail, more particular descriptions of the invention may be had by reference to certain embodiments which are illustrated in the appended drawings. These drawings form a part of the specification. It is to be noted, however, that the appended drawings illustrate preferred embodiments of the invention and therefore are not to be considered limiting in scope.

FIG. 5 shows component vesicles (V) and ribosome-sized granules. An arrow indicates the free surface of the retentate.

DETAILED DESCRIPTION OF THE INVENTION

Figure 1:
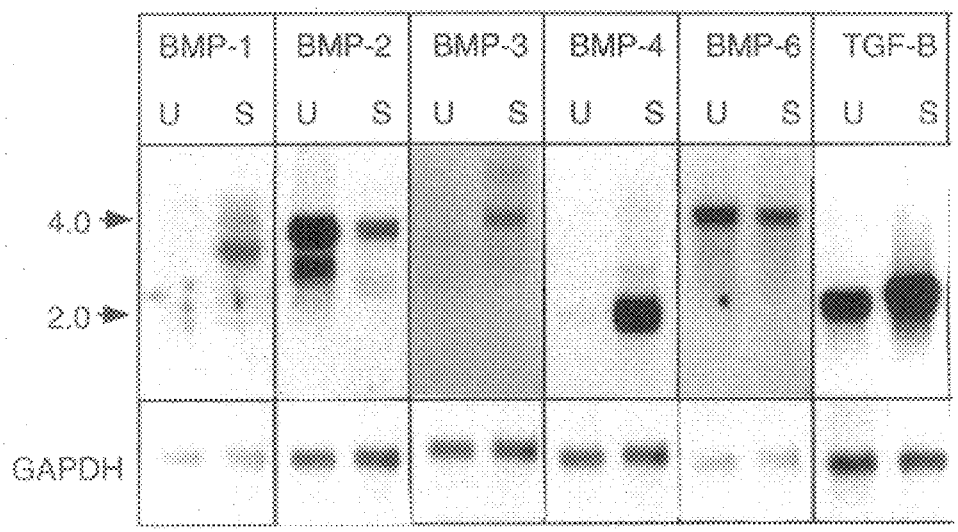
FIG. 1 shows the northern blot analysis of BMP-1 through BMP-4, BMP-6 and TGF-$\beta$ mRNA in non-bone-inducing U2OS cells (designated U) versus the osteoinductive Saos-2 cells (designated S).

Craniofacial defects result from incomplete endochondrial bone development, while inadequate membrane bone formation is the underlying defect in osteogenesis imperfecta. An understanding of embryonic signaling molecules that regulate bone development can lead to methods to promote bone growth in these diseases.

In this connection, a bone inducing agent (BIA), extractable from mass-cultured Saos-2 human osteosarcoma cells, has recently been uncovered which can stimulate the growth of new bone with marrow in soft tissues of recipient animals. It has also been shown that implants of semipurified bone-inducing agent can accelerate greatly the healing of large bone defects in rats. In trying to understand the mechanism by which the Saos-2 cell bone-inducing agent can induce bone formation, it has been shown that these cells express high levels of bone morphogenetic proteins (BMPs-1,2,3,4,6 (30,31). The bone morphogenetic proteins regulate embryonic bone development, and also are involved in early embryonic patterning (21,25). Preliminary studies with bone inducing agents also suggest that molecules in addition to bone morphogenetic proteins may be required to stimulate new bone formation in vivo by osteoprogenitor cells (8,17, 44). The bone-induction process is a recapitulation of the multifactorial process of bone formation as seen in embryonic limbs, in fracture repair, and in the surgical promotion of bone growth in craniofacial defects.

The present invention demonstrates that human Saos-2 cells generate and secrete an osteoinductive agent of a protein nature that can be isolated and purified by methods currently available for protein purification. Analysis of purified preparations of Saos-2 cell products suggests that bone induction by this agent is multifactorial; i.e., that osteoinduction requires the interaction of more than one, and probably several component proteins in a cascade-like reaction, rather than the action of a single protein. There are as yet unrecognized bioactive protein(s), other than bone morphogenetic proteins, in Saos-2 cell extracts that may participate in the mechanism of osteoinduction.

A bone-inducing agent has been discovered in extracts of the Saos-2 strain of cultured human osteosarcoma cells (5,13). This bone inducing agent can induce the formation of entirely new bones in soft tissues where they do not normally occur, and has been shown to dramatically improve the rate of healing of large bone defects in rats (20).

Characteristics of the bone inducing Saos-2 osteosarcoma cells are as follows: 1) they were cultured originally from an osteosarcoma of an 11 year old female human patient (13); 2) they can be propagated in mass culture using methods already developed; 3) they did not grow or form tumors in nude mice (13); 4) they are osteoinductive either as devitalized cells or as extracts; 5) Saos-2 cells or their extracts are non-toxic to recipient animals.

Concerning bone induction by Saos-2 cells or extracts thereof, Saos-2 cells represent a concentrated source of bone inducing activity. The amount of bone inducing agent present in only $5 \times 10^6$ to $10 \times 10^6$ Saos-2 cells is sufficient to induce endochondrial bone formation in virtually 100% of nude mouse implants. This amount of crude bone inducing agent is equivalent to the activity contained in approximately 2.5 mg of freeze dried cells or 300 micrograms of GuHCl extract. There is no necessity to utilize living Saos-2 cells for bone induction. Saos-2 cells do not survive transplantation into Nu/Nu mice (13) and presumably would not grow in human recipients even if implanted live.

Initial attempts to isolate the bone inducing agent from a GuHCl extract of Saos-2 cells by gel filtration on sephadex G200 showed that bone inducing activity is concentrated about five to ten-fold in fractions with a molecular weight range of 10 to 50 kilodaltons. Freeze-dried, acetone-defatted Saos-2 cells or GuHCl-extracts alone induce the full sequence of endochondral bone in Nu/Nu mice after intramuscular implantation, either with or without adding a carrier of pure collagen. Thus there is no requirement for a carrier of incompletely defined bone matrix, nor for any other additive, such as TGF-β to support osteoinduction.

Saos-2 cells can be mass cultured in roller bottles with a cell doubling time of approximately 36 hours and with complete preservation of bone inducing activity using DMEM medium plus 10% fetal calf serum. Saos-2 cells can be grown in a defined serum-free medium (Ventrex PC-1) without loss of osteoinductive activity. Protein concentrated from serum-free culture medium that had been exposed for 48 hours to confluent Saos-2 cells induces bone formation. Thus, Saos-2 cells release bone inducing agent into the culture media. In the experiments, conditioned medium is used as an alternative source of bone inducing agent for purification.

Figure 2:
FIG. 2 shows the immunofluorescent expression of BMP-4 protein in the cytoplasm of Saos-2 cells

Experiments were carried out to determine whether already identified osteoinductive factors—e.g., the bone morphogenetic proteins and/or TGF-β—are expressed by Saos-2 cells. This might explain the Saos-2 cells' osteoinductive capability. Northern blot analysis of mRNA from confluent cells revealed strong expression of BMP-1,-2,-3,-4,-6 and TGF-β mRNA by Saos-2 cells (FIG. 1A). Surprisingly, non-osteoinductive U2OS human osteosarcoma cells also expressed all of the above except BMP-1, plus higher levels of BMP-2 and trace amounts of BMP-5 and 7, not seen in Saos-2 cells (30,31). Western blots and the ROS cell bioassay confirmed the presence of TGF-β protein in both Saos-2 and U2OS cells. Immunofluorescence has detected the presence of BMP-1 and 4 proteins in the cytoplasm of Saos-2 cells (FIG. 2). Saos-2 cells may contain an optimal admixture of bone morphogenetic proteins plus perhaps other unknown factors (not expressed in U2OS cells), which interact to induce bone. The fact that two similar human osteosarcoma cell lines express mRNA for several BMPs but differ in osteoinductive ability suggests that the mere expression of mRNAs or proteins for one or a few of the BMPs may be present but not necessarily be sufficient for de novo bone formation and fracture healing.

Figure 3A:
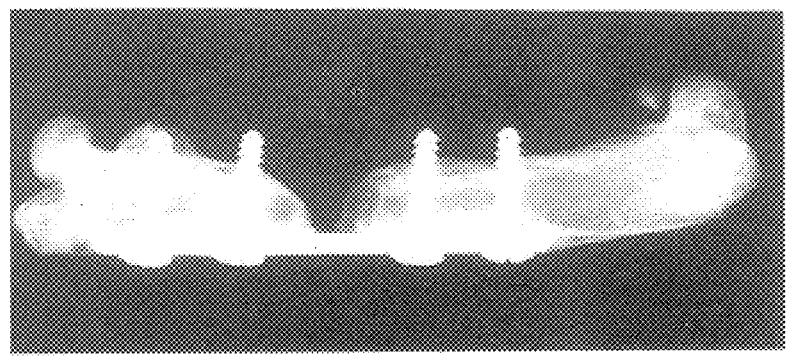
FIGS. 3A and 3B show a comparison of the extent of healing in large surgical defects of rat femur at 8 weeks after surgery. The animal depicted in FIG. 3A received no implant. The animal depicted in FIG. 3B received an implant containing 10 mg bone-inducing agent extracted from Saos-2 cells plus 10 mg of collagen. In this experiment, only the bone inducing agent-containing defects healed completely by bony union, whereas none of the control implants lacking the bone-inducing agent healed.
Figure 3B:
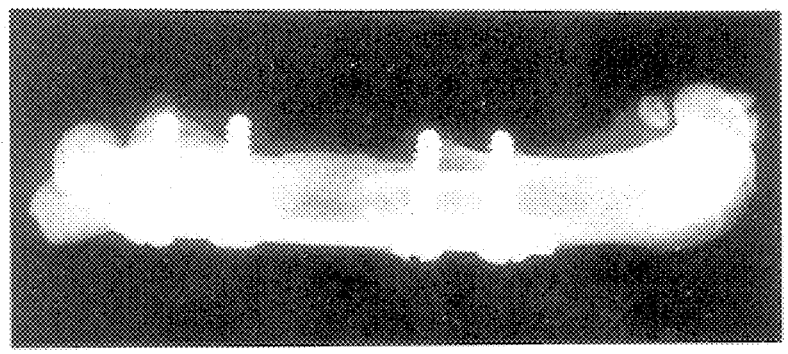

The ability of semipurified Saos-2 bone-inducing agent to promote bone repair was examined in non-healing surgical defects in adult rat femurs. Adult Long Evans rats were divided into 4 groups of 5 rats each as follows: group 1=non-implant control; group 2=defect filled with purified bovine collagen (vitrogen); group 3=defect filled with granules of autografted bone, and; group 4=defect filled with a 50:50 mixture of semipure bone-inducing agent plus purified bovine collagen. At 8 weeks, four out of five animals implanted with bone-inducing agent showed complete bony union (FIGS. 3A–B). Animals in groups 1 and 2 showed little or no healing, and healing was incomplete in the defects with autograft.

The present invention provides a method of isolating a bone inducing agent in vitro, comprising the steps of: growing Saos-2 cells; harvesting said Saos-2 cells; pelleting said Saos-2 cells; washing said Saos-2 cells in acetone; drying said Saos-2 cells; dissolving said Saos-2 cells in GuHCl; centrifuging said dissolved Saos-2 cells at about 10,000 g to produce a pellet and a supernatant; running said supernatant through a Sephacryl 200 column in GuHCl to produce a first eluate; collecting fractions of said first eluate; pooling said fractions of said first eluate to produce a first pooled protein fraction, wherein said fractions pooled contain a highest bone inducing activity; dialyzing said first pooled protein fraction against about 6M urea to produce a first dialysate; running said first dialysate through an anion or cation exchange column to produce a second eluate; collecting fractions of said second eluate; pooling said fractions of said second eluate to produce a second pooled protein fraction, wherein said fractions pooled contain a highest bone inducing activity; running said a second pooled protein fraction through a Heparin/Sepharose column to produce a third eluate; collecting fractions of said third eluate; pooling said fractions of said third eluate to produce a third pooled protein fraction, wherein said fractions pooled contain a highest bone inducing activity; dialyzing said third pooled protein fraction to produce a second dialysate; applying said second dialysate to an HPLC column; eluting said second dialysate by an acetonitrile gradient; collecting fractions of said second dialysate; and pooling said fractions of said second dialysate to produce a fourth pooled protein fraction, wherein said fractions pooled contain isolated bone inducing agent.

In addition, the present invention provides a method of isolating a bone inducing agent in vitro, comprising the steps of: growing Saos-2 cells to confluence in an appropriate cell culture medium with serum; removing said cell culture medium with serum; washing said Saos-2 cells; adding an appropriate cell culture medium without added serum; incubating said Saos-2 cells for about 48 hours; collecting said cell culture medium without added serum; and filtering said cell culture medium without added serum through a 0.45 micron pore filter to produce a filtrate and a retentate; wherein said retentate contains said isolated bone inducing agent. A particular embodiment of this method further includes the steps of: solublizing said retentate in about 6M urea and dialyzing said solublized retentate against water to produce dialyzed retentate.

Another object of the present invention is to provide a method of augmenting bone growth locally comprising implanting the bone inducing agent isolated in the above-detailed methods, together with a mechanically suitable biodegradable carrier, near osteoprogenitor cells selected from the group of marrow, periosteum amd endosteum.

The following examples are given for the purpose of illustrating various embodiments of the invention and are not meant to limit the present invention in any fashion.

EXAMPLE 1

Isolation and Purification of Bone Inducing Agent

Most of the osteoinductive activity of free-dried Saos-2 cells can be extracted into either 4M GuHCl or 6M urea. The sequence of steps for initial purification follows steps used by those skilled in the art in bone morphogenetic protein isolation. Gel filtration is placed first in the method of the present invention because Sephacryl S200 can concentrate the activity of bone inducing agents in the 10 to 50 kD molecular weight range about 5 to 10 fold.

Purification protocol:

a. Extraction: Acetone-dried cell pellets are dissolved in 4M GuHCl and then centrifuged at 10,000×g for 15 minutes. Supernatants containing solubilized bone inducing agents are used in the following chromatographic steps.

b. Sephacryl 200 chromatography: The GuHCl extract is applied to a Sephacryl 200 column in the presence of 4M GuHCl. Fractions containing the highest bone inducing agent activity (Table I) are pooled.

c. Cation exchange chromatography: The pooled active fractions from Sephacryl 200 are dialyzed against 6M urea and then applied to a Biorex column in the presence of urea. Proteins are eluted with a gradient of NaCl from 10 mM to 500 mM. Fractions containing highest bone inducing agent are pooled.

d. Heparin-Sepharose chromatography: The pooled active fractions from cation (or anion) exchange are applied to a Heparin-Sepharose column in the presence of 6M urea. The column is eluted with a gradient of 0.1–0.5M NaCl. The active fractions are pooled and dialyzed against 30% acetonitrile and 0.1% trifluoacetic acid.

e. Reversed Phase HPLC chromatography: The dialyzed heparin sepharose fractions are applied to an HPLC column (C-18 Vydac, 5 μm particles, pore size 300 Å). Proteins are eluted by a gradient of acetonitrile ranging from 5–70%. The active fractions are pooled. Alternatively, as starting material, the water-soluble protein concentrated from serum-free conditioned media filtrate, or 6M urea-solubilized conditioned media protein retained on 0.45 micron filters are used. As indicated above, this apparently soluble filtrable protein fraction, released by Saos-2 cells into culture medium, contains a significant level of bone inducing agent activity.

TABLE I

| Fraction mol. wt range | Mg of fraction implanted | ALP total U/implant | ALP U/mglage protein | Carti- | Bone |
|---|---|---|---|---|---|
| 80–200 kDa | 1.0 | .602 | .226 | ++ | ++ |
| " | .3 | .004 | .002 | 0 | 0 |
| " | .1 | .002 | .001 | 0 | 0 |

TABLE I-continued

| Fraction mol. wt range | Mg of fraction implanted | ALP total U/implant | ALP U/mglage protein | Carti- | Bone |
|---|---|---|---|---|---|
| 60–80 kDa | 1.0 | 1.099 | .389 | ++ | ++ |
| " | .3 | .025 | .007 | 0 | 0 |
| " | .1 | .004 | .002 | 0 | 0 |
| 50–60 kDa | 1.0 | .854 | .262 | 0 | + |
| " | .3 | .033 | .012 | 0 | 0 |
| " | .1 | .022 | .006 | 0 | 0 |
| 40–50 kDa | 1.0 | 1.157 | .485 | + | +++ |
| " | | .241 | .107 | + | 0 |
| " | | .016 | .007 | 0 | 0 |
| 30–40 kDa | 1.0 | 2.125 | .748 | + | +++ |
| " | .3 | .003 | .001 | 0 | 0 |
| " | .1 | .002 | .001 | 0 | 0 |
| 10–30 kDa | 1.0 | 1.255 | .476 | ++ | +++ |
| " | .3 | .085 | .027 | ++ | ++ |
| " | .1 | .014 | .004 | 0 | 0 |

TABLE I shows the results of a typical gel filtration of a GuHCl extract of Saos-2 cells. The most concentrated bone inducing agent activity elutes in the 10–50 kDa range, in which fraction a minimum dose of 0.3 mg of extracted protein can induce bone formation. This minimum dose level indicates an approximate 10 fold concentration of bone-inducing activity over the level of activity seen in unextracted freeze-dried Saos-2 cells where the minimum dose required for bone induction is approximately 2.5 mg. (+=a little, ++=a moderate amount, +++=a maximal amount.)

EXAMPLE 2

Biochemical and Immunological Characterization of Bone-inducing Agents

Active fractions obtained during purification were examined for degree of purity; i.e., the presence of just one or a few major proteins using SDS-polyacrylamide gel electrophoresis (PAGE). The isoelectric point (pI) of the putative bone-inducing agent was determined by isoelectric focusing and related to elution behavior in ion-exchange chromatography. The possible presence in the fractions of interactive cytokine(s); e.g., TGF-β was monitored by western blot techniques using commercially available antisera. At the point where bone inducing agent activity appears to reside in one or two bands of protein in SDS-PAGE, the bands were isolated and N-terminal amino acid sequencing carried out to determine the degree of homology to other known bone morphogenetic proteins.

Western blot techniques were used to address the presence and prevalence of known bone morphogenetic proteins in extracts and in sequentially purified fractions of Saos-2 cells or media. For example, antibodies for BMP-1 (from Dr. P. Reynolds, et al.), BMP-4 (using monoclonal antibody to human BMP-4, supplied by Dr. K. Masuhara of Osaka University) and BMP-6 (supplied by Dr. Steve Gitelman of U.C. San Francisco were used). BMP-1, BMP-3 and BMP-4 are expressed in higher amounts by Saos-2 cells than by the non-osteoinductive U2OS cells (7,29, 30). The presence of these proteins is assessed additionally by immunofluorescent and immunoperoxidase staining of the Saos-2 cells. (FIG. 2 above shows the results of a study to immunolocalize BMP-4.)

EXAMPLE 3

Ability of Saos-2 Cell Proteins to Stimulate Bone Differentiation In Vitro

Certain BMPs have been shown to stimulate the expression of osseous phenotypic traits by cultured marrow stromal osteoprogenitor cells (31). Also, preosteoblastic cell lines have been induced by BMPs to express alkaline phosphatase (ALP) and other molecular markers of bone cell differentiation. These include primary rat osteoblast cells by BMP-2 or BMP-3 (9,39,43,48), and W-20-17 or C3H, 10T1/2 pluripotent mouse mesenchymal stem cells (23,60). Exposure to purified extracts of Saos-2 cells or fractions derived from Saos-2 cell conditioned culture media is capable of stimulating osseous differentiation by one or more of these cells. Establishing a system of in vitro bone induction using the Saos-2 cell bone-inducing agent provides a more quantifiable bioassay method for testing the osteoinductivity of various fractions and isolates of bone inducing agent. Furthermore, such an in vitro assay is ideal to study the mechanism of osteoinduction under defined conditions at the cellular level, e.g., bone inducing agent receptors, method of signal transduction, etc.

First, an in vitro system is devised in which partially or completely solubilized preparations of bone inducing agent are used to stimulate osteoblastic differentiation in first passage cultures of rat marrow stromal cells. Markers for osseous differentiation include 1) expression of ALP in stromal cells and media; 2) enhanced synthesis of proteoglycan in the presence of bone inducing agent as occurs in limb bud mesenchymal cell culture exposed to BMP-3; 3) increased number of bone nodules developing per unit area of culture surface; and 4) $CaPO_4$ deposition by bone nodules, measured as the number of VonKossa positive nodules per unit area of culture surface. As a positive control, $10^{-9}$ to $10^{-8}$ M dexamethasone is added to the culture medium. Dexamethasone initiates reliably osseous phenotypic expression in rat marrow stromal cell cultures.

Initially, isolates of bone-inducing agent which are soluble or partially soluble are added to the medium of stromal cell cultures to try to augment osseous differentiation. These preparations include the apparently soluble protein concentrated from serum-free Saos-2 cell conditioned medium which recently has been found to contain bone-inducing agent activity. The dialyzed urea extract of Saos-2 cells is also examined. After dialysis, bone-inducing agent activity usually remains dissolved (or finely suspended) in the aqueous phase. Increasing concentrations of conditioned medium protein or of dialyzed urea extract of Saos-2 cells (10 to 300 Mg/ml) are added to the cultured cells. On days 1, 3 and 6 the monolayers are washed twice in PBS and scraped into either deoxycholate buffer prior to protein and ALP measurements, or into 4M GuHCl to extract proteoglycan prior to its measurement as hexosamines. Test cultures are allowed to grow for 5–14 days, at which point 10 mM β-glycerophosphate (βGP) is added to the culture medium to promote the calcification of incipient bone nodules. After an additional 5–9 days of cultivation, the stromal cell cultures are terminated by fixing in buffered 10% formalin and stained by the VonKossa silver method prior to microscopic counts of calcified bone nodules. To provide positive control cultures, $10^{-9}$ to $10^{-8}$ M dexamethasone is added to the culture medium to induce cultured bone nodules. Primary cultures of rat marrow stromal cells can be released by mild trypsin, aliquotted into DMSO-containing medium, and frozen indefinitely until first passage sub-culture. First passage cultures, taken out of liquid nitrogen, grow well in the standard alpha MEM medium containing 10 to 15% fetal calf serum (FCS), and respond to $10^{-8}$ M dexamethasone by increasing expression of ALP and by elaborating numerous calcificable bone nodules. However, they do not show osseous differentiation if dexamethasone is withheld.

If bone-inducing agent-containing protein from conditioned medium or the urea extract of Saos-2 cells fails to induce osseous differentiation by marrow stromal cells, it could be due to a lack of responsiveness of these cells to the semi-purified bone inducing-agent provided, or it could be due to the fact that ideal in vitro conditions have not been provided to support induction of the osseous phenotype. One concern may be that the bone inducing agent is insufficiently soluble to be able to activate osseous differentiation in these cells. More intimate contact between stromal cells and bone-inducing agent containing extracts can be accomplished by growing stromal cells on a substratum composed of either Matrigel, collagen or clotted human fibrinogen into which the bone inducing agent-containing protein fractions have been dispersed as a fine suspension. If bone-inducing agent is sparingly soluble in vitro, as it appears to be in in vivo, then it should be slowly released over hours to days into the immediate vicinity of the cultured stromal cells growing in such a 3-dimensional arrangement. Co-cultures of marrow stromal cells and Saos-2 cells also are used to see whether the former is stimulated to osseous differentiation upon cell to cell exposure to bone inducing agent-producing Saos-2 cells.

If marrow stromal cells are persistently unresponsive to bone inducing agent preparations, an inducible pluripotent cell line, such as C3H 10T 1/2 mouse cells, is used. This cell line was recently shown by Katagiri, et al. (23) to express a 15-fold increased ALP in the presence of only 1 microgram/ml of BMP-2A. These 10T1/2 cells are available from the laboratory of Dr. Arnold Kahn at the University of California, San Francisco where the cell line was originated. The C3H 10T1/2 cells are grown on a collagenous tissue culture substratum that is impregnated with varying concentrations of semi-purified bone inducing agent, either in solution or as a fine particulate suspension in a gel substratum. Thus, the test cells are growing in intimate contact with bone inducing agent (10 to 100 μg bone inducing agent per 35 mm tissue culture dish). At intervals of up to two weeks the cultured cells are released from attachment by collagenase. The specific activity of ALP is tested in deoxycholate extracted cells and in the culture supernatant. The cultures are observed microscopically on a daily basis to determine whether any calcified bone nodules appear, as occurs when primary rat osteoblasts or marrow stromal cells are stimulated by $10^{-8}$ dexamethasone in the presence of 10 mM β-glycerophosphate.

EXAMPLE 4

Secretion of Bone-Inducing Agent by Cultured Human Osteosarcoma Cells

An extractable bone-inducing agent was identified in Saos-2 cultured human osteosarcoma cells. These cells can be mass cultured, thus providing an abundant, self-renewing source of bone-inducing agent. Saos-2 cells express bone morphogenetic proteins-1, 2, 3, 4, 6 and TGF-β (7,30,31), any or all of which may play a role in osteoinduction (7,28,47). Also, implants of Saos-2 cell extracts promoted rapid healing of large bone defects in rat femurs (20). The present invention demonstrates that Saos-2 cells secrete bone-inducing agent into their culture medium as well as retaining it intracytoplasmically and differentiates whether secreted bone-inducing agent is soluble or particulate.

Figure 4:
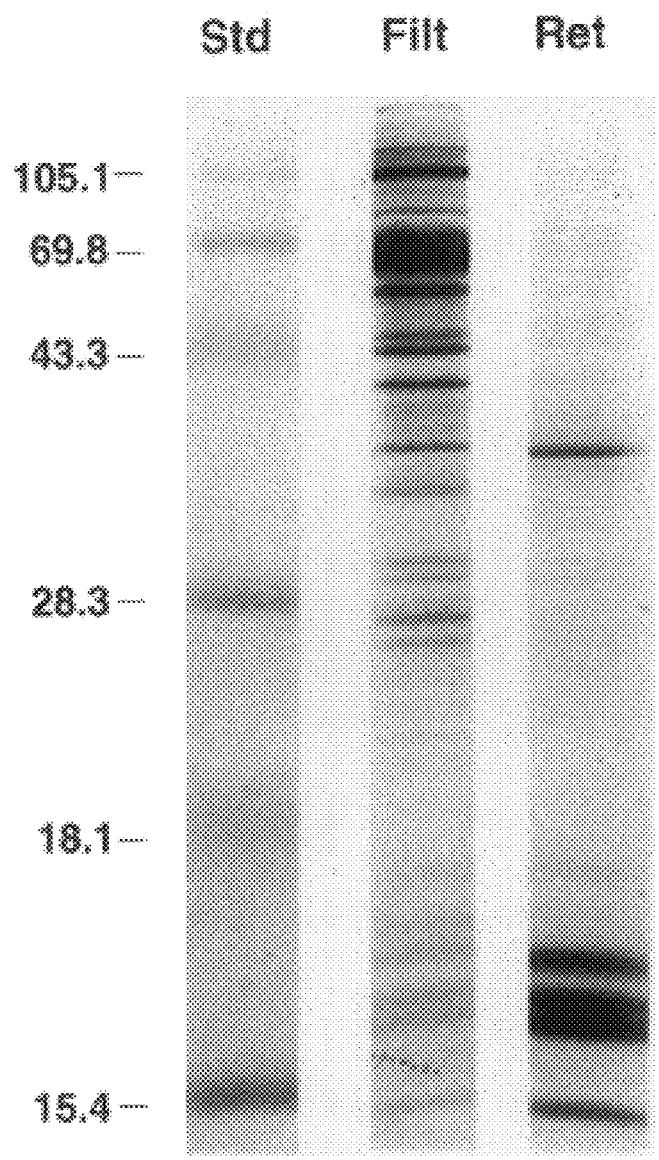
FIG. 4 shows an SDS gel electrophoresis of Coomassie-stained proteins. 1) Molecular weight standards; 2) Saos-2 conditioned media "filtrate" which passed through a 0.45 $\mu$m pore size filter; 3) Saos-2 conditioned media "retentate" retained by 0.45 $\mu$m pore size filter. Molecular weights are indicated on the ordinate in kilodaltons. SDS gel electrophoresis showed predominantly high molecular weights (20 to 100 kDa) in the filtrate and predominantly low molecular weight proteins (15 to 30 kDa) in the retentate.
Figure 5:
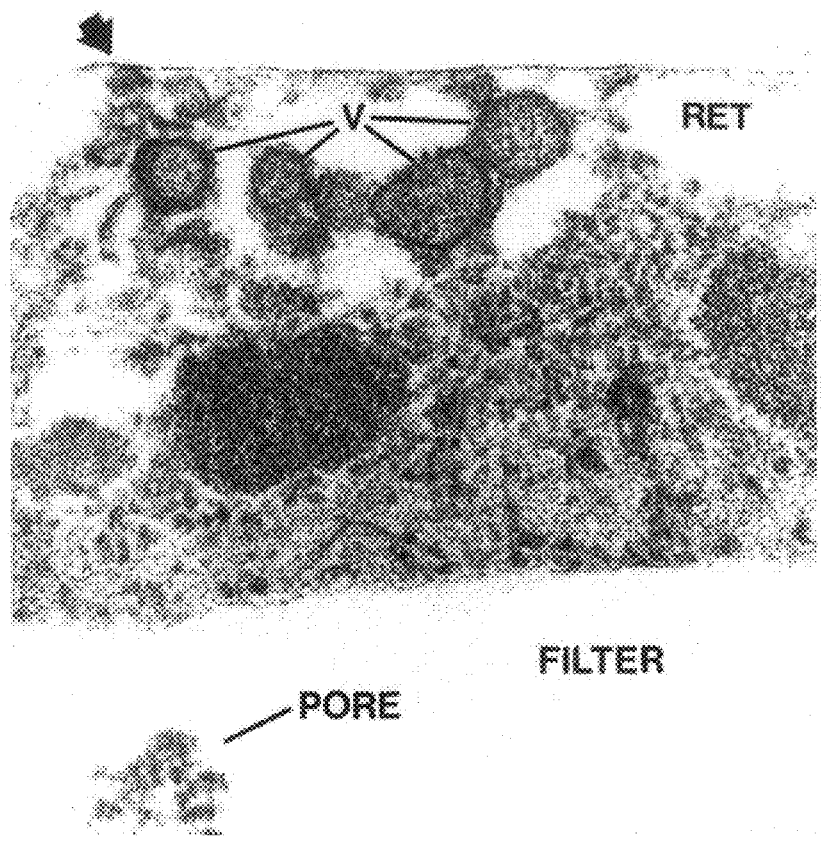
FIG. 5 shows an electron microscopic structure of retentate (RET) on the surface of a 0.45 micron filter.
Figure 6:
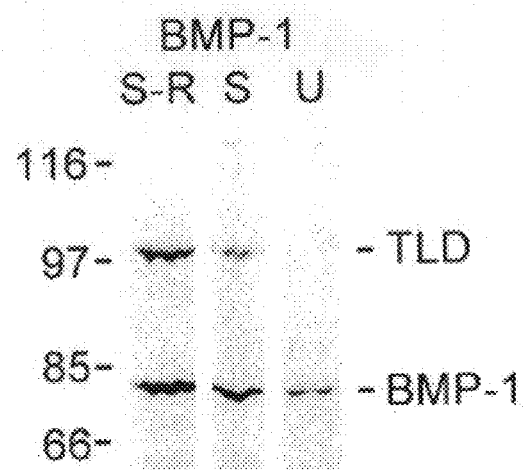
FIG. 6 shows the results of a western blot showing both BMP-1 (84 kD) and tolloid (97 kD) proteins in Saos-2 cell conditioned media retentate (lane 2), GuHCl extract of Saos-2 cells (lane 3), and acetone extract of Saos-2 cells (lane 4). Non-osteoinductive U2OS cells (lane 5) show only a trace of BMP-1 protein while tolloid is undetectable. Molecular weights are indicated in kD at the ordinate.
Figure 7:
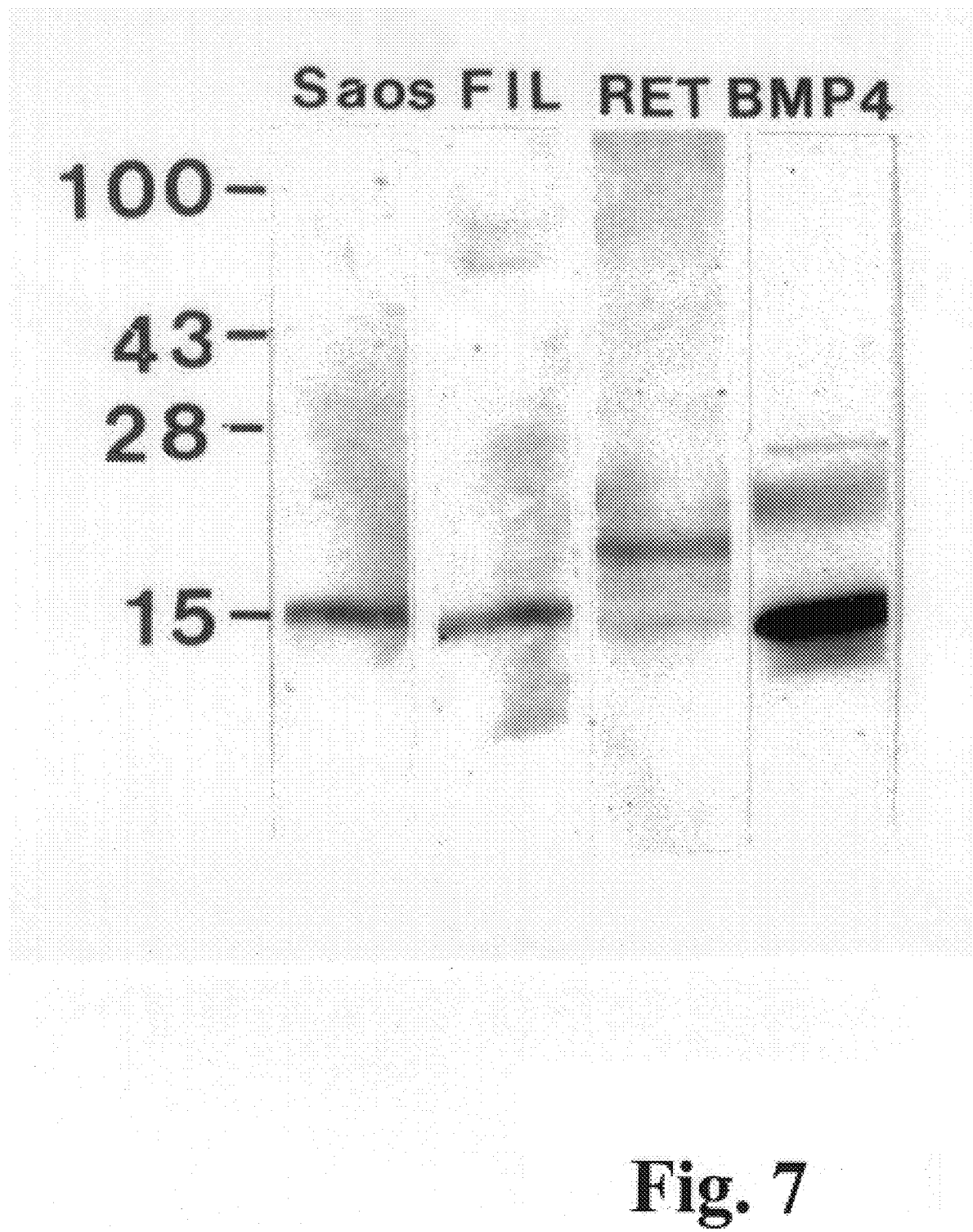
FIG. 7 reveals the results of a chemiluminescent western blot showing the most immunoreactive BMP-4 at approximately 15 kD in a GuHCl extract of Saos-2 cells (lane 1), in a filtrate of Saos-2 conditioned media (lane 2), and in control recombinant human BMP-4 (lane 4). Saos-2 conditioned media retentate (lane 3) shows a prominent immunoreactive band at approximately 18 Kd plus a faint band at 15 Kd.

Saos-2 cells were grown to confluence in Dulbecco's minimal essential medium (DMEM) with 10% fetal calf serum. At confluence, the cells were overlaid with serum-free DMEM for 48 hours. This conditioned medium was filtered through 0.45 μm pore filters to retain any vesicular microsomes ("retentate"). The filtrate was concentrated to about 20% of its original volume, and bioassayed for osteoinductivity by implanting 1 to 10 mg of filtrate protein mixed with 2 mg purified bovine collagen (Vitrogen, Collagen Corp.) as a freeze dried pellet in the back muscles of Nu/Nu mice. The filter "retentate" was solubilized in 6M urea, and then dialyzed against $H_2O$. The dialysate was freeze-dried with 2 mg of bovine collagen and bioassayed. New cartilage and bone induced at 14 days was evaluated by microscopy and quantitated by measuring total and specific alkaline phosphatase (ALP) activity. Filtrate and retentate protein was characterized by reduced SDS polyacrylamide gel electrophoresis (SDS-PAGE) (FIG. 4), and the retentate was examined by transmission electron microscopy (FIG. 5). In recent studies, the presence of BMP-1/tolloid proteins (FIG. 4) and BMP-4 protein (FIG. 5) has been demonstrated by Western blot in extracts of Saos-2 cells and in the highly osteoinductive retentate fraction of Saos-2 cell conditioned media (FIGS. 6 and 7).

The filtrate protein was osteoinductive in 6 of 8 implants (3 mg; 75%) (mean ALP specific activity+SD=0.239±0.140 units) and in 2 of 6 one mg implants (33%) (mean ALP= 0.103±0.165 units). The retentate protein, was even more osteoinductive than the filtered media protein, i.e., bone and/or cartilage was induced in 7 of 7 three mg implants (100%) (mean ALP=0.800±0.378 units), and 5 of 5 (100%) 1 mg samples (mean ALP=0.490±0.642 units). SDS-PAGE showed predominantly high molecular weight proteins (20 to 100 kDa) in the filtrate and predominantly low molecular weight proteins (15 to 30 kDa) in the retentate (FIG. 4). Transmission electron microscopy of the retentate showed vesicles similar in ultra-structure to skeletal matrix vesicles (4) plus dense granular non-membrane particles (FIG. 5).

The present invention is the first report that osteoinductive Saos-2 human osteosarcoma cells secrete a bone-inducing agent as well as retaining bone-inducing agent intracytoplasmically. Also, this is the first indication that osteoinductive bone-inducing agent proteins are present as an aqueous component of Saos-2 conditioned media. These findings provide insight into the manner by which bone cells, such as Saos-2, metabolize osteoinductive substances. It has been presumed that BMPs are mainly secreted into the bone matrix, however, the possibility remains that osteoinductivity might reside in residual cells and cell fragments rather than in decalcified matrix per se. The present invention demonstrates that there is both cellular retention and secretion of osteoinductive substances by Saos-2 cells. The fact that a component of bone-inducing agent is concentrated in exocytosed vesicles and subcellular particles suggests that extracellular "matrix vesicles", which are known to initiate calcification (4), may also function in bone induction and repair.

EXAMPLE 5
Relevance to Orthopedic and Birth Defects

Possible clinical orthopedic uses for the Saos-2 bone-inducing agent include the following:

(1) Promotion of fusion between vertebral bodies in spine repair operations such as Harrington rod implacement for treatment of scoliosis, or to promote spinal fusion after intervertebral disc removal. In these operations, significant amounts of iliac crest bone and marrow are currently being used as autograft to promote spine fusion. The post-operative morbidity and discomfort from large-scale iliac crest removal could be avoided by use of a bone-inducing agent mixed with a mechanically suitable biodegradable carrier material and implanted near responsive osteoprogenitor cells of the marrow, periosteum and/or endosteum.

(2) Implantation of Saos-2 cell bone-inducing agent into large surgical bone defects to augment bone growth locally. Such defects are frequently required for successful removal of malignant neoplasms, especially in limb sparing operations for bone cancer.

(3) Implantation of bone-inducing agent derivatives between bone edges to promote the repair of non-union fractures, and/or speed the healing of fractures in the elderly, e.g., hip fractures.

(4) Promotion of bone healing in reparative surgery for large maxillofacial defects.

(5) Use of bone-inducing agent to promote bone ingrowth at the interface between bone and an intraosseous implant. In hip replacement the failure to achieve bonding on an internal prosthesis ("artificial hip") to adjacent bone often leads to loosening of the prosthesis and requires later surgical intervention.

In relation to birth defects, the sequence of development steps in Saos-2 cell bone-induction exactly recapitulates the process of bone formation in embryonic limbs and in healing fractures. Thus it is likely that regulatory factors operating in Saos-2 cell stimulated bone-induction will be similar to factors controlling embryonic limb development and/or fracture healing. An understanding of the mechanism of induction by Saos-2 cell protein will shed light on mechanisms of embryonic bone development and repair. Second, when it is defined and purified, the bone-inducing agent from Saos-2 cells is used as a therapeutic agent to promote normal bone development in clinical situations where development is abnormal, e.g., to promote closure of cleft palates or to augment the surgical repair of craniofacial defects.

There are several potential advantages to using cultured Saos-2 cells as a source of bone inducing agent. Such cells are of human origin, thus reducing the risk of sensitization to foreign proteins when extracts are used therapeutically in humans. The Saos-2 cell line is permanently established and can be grown indefinitely in mass culture to produce large quantities of bone inducing agent, probably at lower cost than with recombinant methods. Bone-inducing activity appears to be quite concentrated in Saos-2 cells, and thus may be more easily extracted from these cells or their media than from transfected hamster cell tissue culture media where the relative concentration of recombinant BMPs may be low and there may be contaminating hamster proteins. The addition of a poorly defined carrier such as GuHCl-extracted, demineralized "bone matrix" is not required to support osteoinduction by Saos-2 cell products because extracts of Saos-2 cells can promote bone healing when combined with a purified and chemically defined collagen carrier (5). Perhaps most importantly, the Saos-2 cells are already genetically programmed by nature to produce an optimal admixture of native human proteins for effective bone development.

The following references were cited herein:
1. Amitani, K., et al., *Gann.*; 66:327–329, 1975.
2. Anderson, H. C., et al., *Am. J. Path.*; 44:507–519, 1964.
3. Anderson, H. C., et al., *Fed. Proc.*; 27:475, 1968.
4. Anderson, H. C., et al., *J. Cell Biol.*; 41:59–72, 1969.
5. Anderson, H. C., et al., *Bone and Min.*; 16:49–62, 1992.
6. Anderson, H. C., *Cur. Opin. Ther. Patents*; 4:17–29, 1994.
7. Anderson, H. C., et al., *Clin. Orthop. Rel. Res.*; 313:129–134, 1995.
8. Bentz, H., et al., *Matrix*; 11:269–275, 1991.
9. Chen, T. L., et al., *J. Bone Min. Res.*; 6:1387–1393, 1991.
10. Cook, S. D., et al., *Spine*; 19:1655–1663, 1994.
11. Dale, L., et al., *Develop.*; 115:573–585, 1992.
12. Elima, K., *Ann. Med.*; 25:395–402, 1993.
13. Fogh, J., et al., In : *Human Tumor Cells It Vitro*, J. Fogh Ed., Plenum, New York pp 115–159. 1975.

14. Francis-West, P. H., et al., *Develop. Dynam.*; 201:168–178, 1994.
15. Fukagawa, M., et al., *Develop. Biol.*; 163:175–183, 1994.
16. Gerhart, T. N., et al., *Clin. Orthop. Rel. Res.*; 293:317–326, 1993.
17. Hammonds, R. G., et al., *Molec. Endocrinol.*; 5:149–155, 1991.
18. Harland, R. M., *Proc. Nat. Acad. Sci.* 91:10243–10246, 1994.
19. Hollinger, J., et al., *J. Oral Maxillofac. Surg.*; 47:1182–1186, 1989.
20. Hunt, T. R., et al., *J. Bone Jt. Surg.*, 78A:41–48, 1996.
21. Jones, C. M., et al., *Develop.*; 111:531–542, 1991.
22. Johnson, E. E., et al., *Clin. Orthop. Rel. Res.*; 277:229–237, 1992.
23. Katagiri, T., et al., *Biochem. Biophys. Res. Comm.*; 172:295–299, 1990.
24. Lovell, T. P., et al., *Clin. Orthop. Rel. Res.*; 243:266–274, 1989.
25. Lyons, K. M., et al., *Genes and Develop.*; 3:1657–1668, 1989.
26. Lyons, K. M., et al., *Develop.*, 109:833–844, 1990.
27. Luyten, F. P., et al., *J. Biol. Chem.*; 264:13377–13380, 1989.
28. Masahara, K., et al., *Bone*; 16:91–96, 1995.
29. Nakase, T., et al., *J. Bone Min. Res.*; 9:605–610, 1996.
30. Raval, P., et al., *J. Orthop. Res.*; 14:180, 1993.
31. Raval, P., et al., *J. Dent. Res.*; 75:1518–1523, 1996.
32. Rickard, D. J., et al., *Develop. Biol.*; 161:218–228, 1994.
33. Ripamonte, V., et al., *Matrix*; 12:369–380, 1992.
34. Sampath, T. K., et al., *J. Biol. Chem.*; 265:13198–13205, 1990.
35. Staehling-Hampton, K., et al., *Cell Growth & Diff.*; 5:585–593, 1994.
36. Suzuki, A., et al., *Proc. Nat. Acad. Sci.*; 37:581–588, 1995.
37. Takaoka, K., et al., *Clin. Orthop. Rel. Res.*; 164:265–270, 1982.
38. Takaoka, K., et al., *Clin. Orthop. Rel. Res.*; 292:329–336, 1993.
39. Takuwa, Ohse, G., et al., *Biochem. Biophys. Res. Comm.*; 174:96–101, 1991.
40. Thies, R. S., et al., *Endocrinol.*; 130:1318–1324, 1992.
41. Toriumi, D. M., et al., *Head Neck Surg.*; 117:1101–1112, 1992.
42. Urist, M. R., et al., *Proc. Soc. Exp. Biol. & Med.*; 173:194–199, 1983.
43. Vukicevik, S., et al., *Biochem. Biophys. Res. Comm.*; 166:750–756, 1990.
44. Vukicevik, S., et al., *Biochem. Biophys. Res. Comm.*; 198:693–700, 1994.
45. Vukicevik, S., et al., *J. Histochem. Cytochem.*; 42:869–875, 1994.
46. Wang, E. A., et al., *Proc. Nat. Acad. Sci.* (USA); 87:2220–2224, 1990.
47. Wozney, J. M., et al., *Exp. Pharm.*; 107:723–748, 1993.
48. Yamaguchi, A., et al., *J. Cell Biol.*; 113:681–687, 1991.
49. Yasko, A. W., et al., *J. Bone Jt. Surg.*; 74A:659–670, 1992.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will appreciate readily that the present invention is well adapted to carry out the objects and obtain the ends and advantages mentioned, as well as those inherent therein. The present examples, along with the methods, procedures, treatments, molecules, and specific compounds described, are representative of preferred embodiments, are exemplary, and are not intended as limitations on the scope of the invention. Changes to those methods and compounds and other uses will occur to those skilled in the art and are encompassed within the spirit of the invention as defined by the scope of the claims.

What is claimed is:

1. A method of isolating a bone inducing agent in vitro, comprising the steps of:

growing Saos-2 cells to confluence in an appropriate cell culture medium with serum;

removing said cell culture medium with serum;

washing said Saos-2 cells;

adding an appropriate cell culture medium without added serum;

incubating said Saos-2 cells for about 48 hours;

collecting said cell culture medium without added serum; and filtering said cell culture medium without added serum through a 0.45 micron pore filter to produce a filtrate and a retentate; wherein said retentate contains said isolated bone inducing agent.

2. The method of claim 1, further including the steps of:

solubilizing said retentate in about 6M urea; and dializing said solubilized retentate against water to produce dialyzed retentate.

3. The method of claim 2, further including the step of freeze drying said dialyzed retentate.

4. The method of claim 3 wherein said dialyzed retentate is freeze dried with bovine collagen carrier protein.

5. A bone-inducing agent comprising an isolated secretion of in vitro culture living Saos-2 cells, said secretion, when filtered through a 0.45 micron pore filter, giving a filtrate and a retentate, said filtrate having predominantly 20–100 kDa proteins therein, said retentate having predominantly 15–18.1 kDa proteins therein.

6. The agent of claim 5, said agent selected from the group consisting of said filtrate and retentate.

7. The agent of claim 6, said retentate being solubilized in urea and dialyzed against water to form a dialysate, said dialysate being freeze-dried with bovine collagen.

8. A method of augmenting bone growth locally comprising implanting the bone-inducing agent of claim 5 near osteoprogenitor cells in an in vivo subject.

9. The method of claim 8, said cells being in a biodegradable carrier.

10. A method of isolating a bone-inducing agent comprising the steps of:

growing Saos-2 cells to confluence in an appropriate cell culture medium, and causing the Saos-2 cells to generate a secretion; and harvesting said secretion, and separating the secretion of said cells.

11. The method of claim 10, said secretion, when filtered through a 0.45 micron pore filter, giving a filtrate and a retentate, said filtrate having predominantly 20–100 kDa proteins therein, said retentate having predominantly 15–18.1 kDa proteins therein.

12. The method of claim 11, including the steps of solubilizing said retentate in urea and dialyzing the solubilized retentate against water to form a dialysate, said dialysate being freeze-dried with bovine collagen.

13. A method of augmenting bone growth locally in vitro comprising the step of implanting an isolated bone inducing agent, together with a mechanically suitable biodegradable carrier, near osteoprogenitor cells selected from the group of marrow, periosteum and endosteum cells, said bone inducing agent being isolated by a method comprising the steps of:

growing Saos-2 cells to confluence in an appropriate cell culture medium with serum;

removing said cell culture medium with serum;

washing said Saos-2 cells;

adding an appropriate cell culture medium without added serum;

incubating said Saos-2 cells for about 48 hours;

collecting said cell culture medium without added serum; and filtering said cell culture medium without added serum through a 0.45 micron pore filter to produce a filtrate and a retentate, wherein said retentate contains said isolated bone inducing agent.

14. The method of claim 13, said isolating method further including the steps of:

solubilizing said retentate in about 6M urea; and dialyzing said solubilized retentate against water to produce dialized retentate.

15. A bone-inducing agent comprising an isolated secretion of in vitro cultured Saos-2 cells, said secretion having been filtered to produce a filtrate and a retentate, said bone inducing agent being selected from the group consisting of said filtrate and said retentate wherein when said secretion is filtered through a 0.45 micron pore filter, the filtrate predominantly comprises 20–100 kDa proteins therein and the retentate predominantly comprises 15–18.1 kDa proteins therein.

16. The agent of claim 15, said retentate being solubilized in urea and dialyzed against water to form a dialysate, said dialysate being freeze-dried with bovine collagen.

17. A method of isolating a bone-inducing agent comprising the steps of:

growing Saos-2 cells to confluence in an appropriate cell culture medium, and causing the Saos-2 cells to generate a secretion; and harvesting said secretion, and separating said secretion from said cells by filtering said secretion through a 0.45 micron pore filter, giving a filtrate and a retentate, said retentate having predominantly 20–100 kDa proteins therein, and said filtrate having predominantly 15–18.1 kDa proteins therein.

18. The method of claim 17, further including the steps of solubilizing said retentate in urea and dializing the solubilized retentate against water to form a dialysate, said dialysate being freeze-dried with bovine collagen.

* * * * *